(12) United States Patent
Aali

(10) Patent No.: US 8,558,050 B2
(45) Date of Patent: Oct. 15, 2013

(54) WOUND SHIELD WITH ENCLOSED VACUUM SPACE

(75) Inventor: Adel Aali, Irvine, CA (US)

(73) Assignee: AALNEX, Inc., Irvine, CA (US)

( * ) Notice: Subject to any disclaimer, the term of this patent is extended or adjusted under 35 U.S.C. 154(b) by 812 days.

(21) Appl. No.: 12/557,346

(22) Filed: Sep. 10, 2009

(65) Prior Publication Data

US 2010/0004611 A1 Jan. 7, 2010

Related U.S. Application Data

(63) Continuation of application No. 11/303,155, filed on Dec. 15, 2005, now Pat. No. 7,601,129.

(51) Int. Cl.
*A61F 13/00* (2006.01)

(52) U.S. Cl.
USPC ............... 602/42; 602/41; 602/54; 128/888; 128/889; 604/289; 604/290

(58) Field of Classification Search
USPC ........... 602/2, 41–42; 604/289, 290, 304–308
See application file for complete search history.

(56) References Cited

U.S. PATENT DOCUMENTS

| | | | |
|---|---|---|---|
| 2,148,882 A | 2/1939 | Scholl | |
| 2,273,873 A * | 2/1942 | Klein | 128/888 |
| 2,305,289 A | 12/1942 | Coburg | |
| 2,367,690 A | 1/1945 | Purdy | |
| 2,443,140 A | 6/1948 | Larsen | |
| 2,443,481 A | 6/1948 | Séné | |
| 3,026,874 A | 3/1962 | Stevens | |
| 3,334,626 A | 8/1967 | Schimmel | |
| 3,610,238 A | 10/1971 | Rich | |
| 4,023,569 A | 5/1977 | Warnecke et al. | |
| 4,181,127 A | 1/1980 | Linsky et al. | |
| 4,212,296 A | 7/1980 | Schaar | |
| 4,252,120 A | 2/1981 | Carpenter | |
| 4,399,816 A | 8/1983 | Spangler | |
| 4,726,364 A | 2/1988 | Wylan | |

(Continued)

FOREIGN PATENT DOCUMENTS

| | | |
|---|---|---|
| DE | 519353 C | 9/1931 |
| DE | 731255 C | 2/1943 |

(Continued)

OTHER PUBLICATIONS

USPTO Notice of Allowance for U.S. Appl. No. 11/303,155, 5 pages (mailed Jun. 12, 2009).

(Continued)

*Primary Examiner* — Kim M Lewis
(74) *Attorney, Agent, or Firm* — Foley & Lardner LLP; Nicola A. Pisano; Christopher C. Bolten

(57) ABSTRACT

A wound shield including a conformable frame to circumscribe a wound and warm water circulating system to maintain a warm environment. Any suitable dressing may be secured over the conformable frame providing separation between the wound and the dressing. The wound frame may provide pressure relief around a wound or pressure sore to permit healing. A conformable frame may be composed of one or more layers of any suitable material and may include adhesive on one or more surfaces to secure the frame to the wound site and or to secure the dressing to the conformable frame.

16 Claims, 9 Drawing Sheets

(56) References Cited

U.S. PATENT DOCUMENTS

| | | |
|---|---|---|
| 4,969,881 A | 11/1990 | Viesturs |
| 4,972,829 A | 11/1990 | Knerr |
| 5,020,547 A | 6/1991 | Strock |
| 5,060,662 A | 10/1991 | Farnswoth, III |
| 5,086,763 A | 2/1992 | Hathman |
| 5,101,837 A | 4/1992 | Perrin |
| 5,215,539 A | 6/1993 | Schoolman |
| 5,264,218 A | 11/1993 | Rogozinski |
| 5,356,372 A | 10/1994 | Donovan et al. |
| 5,376,067 A | 12/1994 | Daneshvar |
| 5,449,340 A | 9/1995 | Tollini |
| 5,456,660 A | 10/1995 | Reich et al. |
| 5,478,308 A | 12/1995 | Cartmell et al. |
| 5,512,041 A | 4/1996 | Bogart |
| 5,527,265 A | 6/1996 | McKeel |
| 5,533,962 A | 7/1996 | Peterman et al. |
| 5,603,946 A | 2/1997 | Constantine |
| 5,695,456 A | 12/1997 | Cartmell et al. |
| 5,702,356 A | 12/1997 | Hathman |
| 5,792,089 A | 8/1998 | Penrose et al. |
| 5,817,145 A | 10/1998 | Augustine et al. |
| 5,843,011 A | 12/1998 | Lucas |
| 5,885,237 A | 3/1999 | Kadash et al. |
| 5,891,074 A | 4/1999 | Cesarczyk |
| 5,899,871 A | 5/1999 | Cartmell et al. |
| 5,947,914 A | 9/1999 | Augustine |
| 5,954,680 A | 9/1999 | Augustine |
| 5,961,480 A | 10/1999 | Augustine |
| 5,964,721 A | 10/1999 | Augustine |
| 5,964,723 A | 10/1999 | Augustine |
| 5,986,163 A | 11/1999 | Augustine |
| 6,000,403 A | 12/1999 | Cantwell |
| 6,005,159 A | 12/1999 | Spier |
| 6,010,527 A | 1/2000 | Augustine et al. |
| 6,013,097 A | 1/2000 | Augustine et al. |
| 6,043,408 A | 3/2000 | Geng |
| 6,045,518 A | 4/2000 | Augustine |
| 6,071,254 A | 6/2000 | Augustine et al. |
| 6,071,304 A | 6/2000 | Augustine et al. |
| 6,080,189 A | 6/2000 | Augustine et al. |
| 6,093,160 A | 7/2000 | Augustine et al. |
| 6,095,992 A | 8/2000 | Augustine |
| 6,110,197 A | 8/2000 | Augustine et al. |
| 6,113,561 A | 9/2000 | Augustine |
| 6,143,945 A | 11/2000 | Augustine et al. |
| 6,168,800 B1 | 1/2001 | Dobos et al. |
| 6,211,426 B1 | 4/2001 | Abrams |
| 6,213,965 B1 | 4/2001 | Augustine et al. |
| 6,213,966 B1 | 4/2001 | Augustine |
| 6,217,535 B1 | 4/2001 | Augustine |
| 6,235,047 B1 | 5/2001 | Augustine et al. |
| 6,267,740 B1 | 7/2001 | Augustine et al. |
| 6,283,931 B1 | 9/2001 | Augustine |
| 6,293,917 B1 | 9/2001 | Augustine et al. |
| 6,320,093 B1 | 11/2001 | Augustine et al. |
| 6,323,386 B1 | 11/2001 | Stapf et al. |
| 6,406,448 B1 | 6/2002 | Augustine |
| 6,407,307 B1 | 6/2002 | Augustine |
| 6,419,651 B1 | 7/2002 | Augustine |
| 6,420,622 B1 | 7/2002 | Johnston et al. |
| 6,420,623 B2 | 7/2002 | Augustine |
| 6,423,018 B1 | 7/2002 | Augustine |
| 6,426,066 B1 | 7/2002 | Najafi et al. |
| 6,436,063 B1 | 8/2002 | Augustine et al. |
| 6,440,156 B1 | 8/2002 | Augustine et al. |
| 6,458,109 B1 | 10/2002 | Henley et al. |
| 6,465,708 B1 | 10/2002 | Augustine |
| 6,468,295 B2 | 10/2002 | Augustine et al. |
| 6,485,506 B2 | 11/2002 | Augustine |
| 6,528,697 B1 | 3/2003 | Knutson et al. |
| 6,569,189 B1 | 5/2003 | Augustine et al. |
| 6,570,050 B2 | 5/2003 | Augustine et al. |
| 6,573,420 B2 | 6/2003 | Staph et al. |
| 6,580,012 B1 | 6/2003 | Augustine et al. |
| 6,585,670 B2 | 7/2003 | Augustine et al. |
| 6,589,270 B2 | 7/2003 | Augustine |
| 6,605,051 B2 | 8/2003 | Augustine |
| 6,626,891 B2 | 9/2003 | Ohmstede |
| 6,641,601 B1 | 11/2003 | Augustine et al. |
| 6,653,520 B1 | 11/2003 | Mouton |
| 6,685,681 B2 | 2/2004 | Lockwood et al. |
| 6,716,235 B2 | 4/2004 | Augustine et al. |
| 6,840,915 B2 | 1/2005 | Augustine |
| 6,921,374 B2 | 7/2005 | Augustine |
| 6,960,181 B2 | 11/2005 | Stevens |
| 6,974,428 B2 | 12/2005 | Knutson et al. |
| 7,012,170 B1 | 3/2006 | Tomaioulo |
| 7,074,982 B2 | 7/2006 | Knutson et al. |
| 7,112,712 B1 | 9/2006 | Ancell |
| 7,118,545 B2 | 10/2006 | Boyde |
| 7,122,046 B2 | 10/2006 | Augustine et al. |
| 7,122,712 B2 | 10/2006 | Lutri et al. |
| 7,135,606 B1 | 11/2006 | Dozier et al. |
| 7,176,343 B2 | 2/2007 | Schlussel |
| 7,183,454 B1 | 2/2007 | Rosenberg |
| 7,276,051 B1 | 10/2007 | Henley et al. |
| 7,601,129 B2 * | 10/2009 | Aali .................. 602/2 |
| 7,619,130 B2 | 11/2009 | Nielsen et al. |
| 7,622,629 B2 | 11/2009 | Aali |
| 2001/0051781 A1 | 12/2001 | Augustine et al. |
| 2002/0007136 A1 | 1/2002 | Narula et al. |
| 2002/0026133 A1 | 2/2002 | Augustine et al. |
| 2002/0029010 A1 | 3/2002 | Augustine et al. |
| 2002/0138030 A1 | 9/2002 | Cavanagh et al. |
| 2003/0009122 A1 | 1/2003 | Veras |
| 2003/0036715 A1 | 2/2003 | Knutson et al. |
| 2003/0088201 A1 | 5/2003 | Darcey |
| 2004/0249328 A1 | 12/2004 | Linnane et al. |
| 2005/0004500 A1 | 1/2005 | Rosser et al. |
| 2005/0010153 A1 | 1/2005 | Lockwood et al. |
| 2005/0070835 A1 | 3/2005 | Joshi |
| 2005/0080372 A1 | 4/2005 | Nielsen et al. |
| 2005/0107732 A1 | 5/2005 | Boyde |
| 2005/0113731 A1 | 5/2005 | Qvist |
| 2005/0148921 A1 | 7/2005 | Hsu |
| 2005/0222528 A1 * | 10/2005 | Weston ........................ 602/1 |
| 2006/0064049 A1 | 3/2006 | Marcussen |
| 2006/0116620 A1 | 6/2006 | Oyaski |
| 2006/0189909 A1 | 8/2006 | Hurley et al. |
| 2006/0235347 A1 | 10/2006 | Aali |
| 2006/0253089 A1 * | 11/2006 | Lin ............................ 604/301 |
| 2007/0041960 A1 | 2/2007 | Freeman et al. |
| 2007/0055205 A1 | 3/2007 | Wright et al. |
| 2007/0142757 A1 | 6/2007 | Aali |
| 2007/0142761 A1 | 6/2007 | Aali |
| 2007/0161937 A1 | 7/2007 | Aali |
| 2007/0161938 A1 | 7/2007 | Aali |
| 2007/0191754 A1 | 8/2007 | Aali |
| 2007/0212959 A1 | 9/2007 | Johnson |
| 2008/0091133 A1 | 4/2008 | Matter |

FOREIGN PATENT DOCUMENTS

| | | |
|---|---|---|
| DE | 1963375 A1 | 6/1971 |
| DE | 9302166 U1 | 7/1994 |
| DE | 29820217 U1 | 5/1999 |
| EP | 0117714 A2 | 9/1984 |
| EP | 1303239 B1 | 10/2007 |
| FR | 2583636 A1 | 12/1986 |
| WO | WO 85/01439 A1 | 4/1985 |
| WO | WO 96/15745 A1 | 5/1996 |
| WO | WO 98/53778 A1 | 12/1998 |
| WO | WO 00/07653 A1 | 2/2000 |
| WO | WO 01/49233 A1 | 7/2001 |
| WO | WO 01/93793 A1 | 12/2001 |
| WO | WO 02/05737 A1 | 1/2002 |
| WO | WO 2005/070480 | 8/2005 |
| WO | WO 2007/011596 A2 | 1/2007 |

OTHER PUBLICATIONS

USPTO Non-Final Office Action for U.S. Appl. No. 11/303,155, 7 pages (mailed Jan. 8, 2009).

(56) References Cited

OTHER PUBLICATIONS

USPTO Non-Final Office Action for U.S. Appl. No. 11/303,155, 9 pages (mailed Jul. 14, 2008).
USPTO Notice of Allowance for U.S. Appl. No. 11/409,364, 7 pages (mailed Jul. 10, 2009).
USPTO Final Office Action for U.S. Appl. No. 11/409,364, 9 pages (mailed Mar. 10, 2009).
USPTO Non-Final Office Action for U.S. Appl. No. 11/409,364, 7 pages (mailed May 22, 2008).
USPTO Advisory Action for U.S. Appl. No. 11/409,364, 3 pages (mailed Apr. 8, 2008).
USPTO Final Office Action for U.S. Appl. No. 11/409,364, 7 pages (mailed Nov. 30, 2007).
USPTO Non-Final Office Action for U.S. Appl. No. 11/409,364, 7 pages (mailed May 31, 2007).
USPTO Non-Final Office Action for U.S. Appl. No. 11/303,463, 10 pages (mailed Mar. 17, 2009).
USPTO Final Office Action for U.S. Appl. No. 11/303,463, 9 pages (mailed Dec. 26, 2008).
USPTO Non-Final Office Action for U.S. Appl. No. 11/303,463, 11 pages (mailed Mar. 18, 2008).
USPTO Non-Final Office Action for U.S. Appl. No. 11/107,452, 11 pages (mailed Mar. 17, 2009).
USPTO Final Office Action for U.S. Appl. No. 11/107,452, 8 pages (mailed Sep. 19, 2008).
USPTO Non-Final Office Action for U.S. Appl. No. 11/107,452, 7 pages (mailed Dec. 4, 2007).
USPTO Non-Final Office Action for U.S. Appl. No. 11/107,452, 8 pages (mailed May 31, 2007).
USPTO Non-Final Office Action for U.S. Appl. No. 11/707,464, 11 pages (mailed Apr. 14, 2009).
USPTO Non-Final Office Action for U.S. Appl. No. 11/707,464, 8 pages (mailed Jun. 27, 2008).
USPTO Final Office Action for U.S. Appl. No. 11/441,702, 12 pages (mailed Apr. 10, 2009).
USPTO Non-Final Office Action for U.S. Appl. No. 11/441,702, 8 pages (mailed Jun. 26, 2008).
USPTO Non-Final Office Action for U.S. Appl. No. 11/441,702, 9 pages (mailed May 1, 2007).
USPTO Final Office Action for U.S. Appl. No. 11/303,463, 10 pages (mailed Apr. 8, 2010).
USPTO Notice of Allowance for U.S. Appl. No. 11/107,452, 5 pages (mailed Apr. 29, 2010).
USPTO Notice of Allowance for U.S. Appl. No. 11/707,464, 5 pages (Mailed Sep. 3, 2010).
USPTO Non-Final Office Action for U.S. Appl. No. 11/707,464, 9 pages (mailed Apr. 14, 2010).
USPTO Notice of Allowance for U.S. Appl. No. 11/441,702, 4 pages (mailed Apr. 12, 2010).
USPTO Final Office Action for U.S. Appl. No. 11/107,452, 8 pages (mailed Dec. 24, 2009).
USPTO Final Office Action for U.S. Appl. No. 11/707,464, 9 pages (mailed Dec. 24, 2009).
USPTO Examiner Interview Summary and Non-Final Office Action for U.S. Appl. No. 11/303,463, 9 pages (mailed Aug. 20, 2009).
USPTO Non-Final Office Action for U.S. Appl. No. 11/441,702, 7 pages (mailed Oct. 27, 2009).
USPTO Notice of Allowance for U.S. Appl. No. 12/416,826, 8 pages (mailed Oct. 7, 2011).
USPTO Non-Final Office Action for U.S. Appl. No. 12/416,826, 16 pages (mailed May 24, 2011).

* cited by examiner

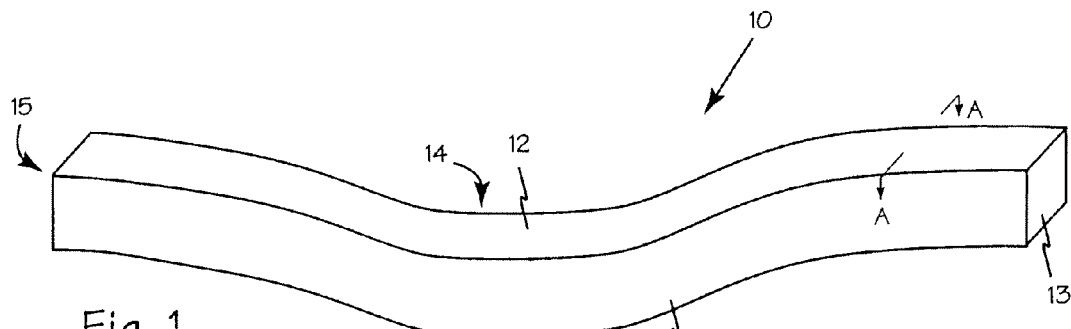
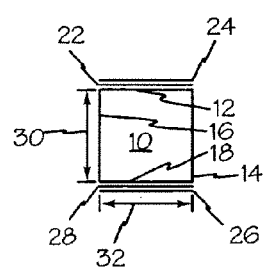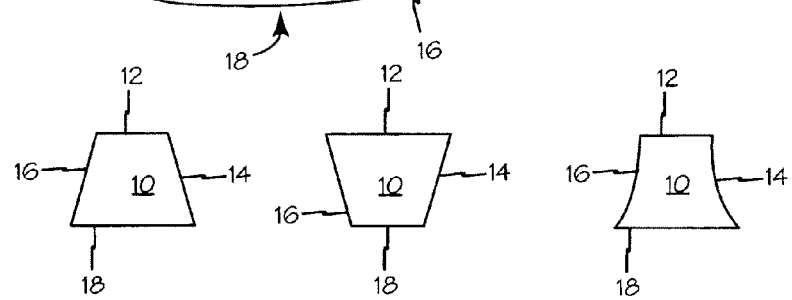
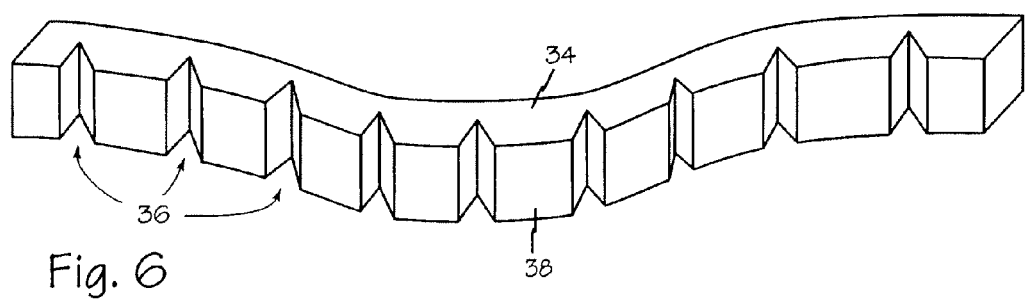
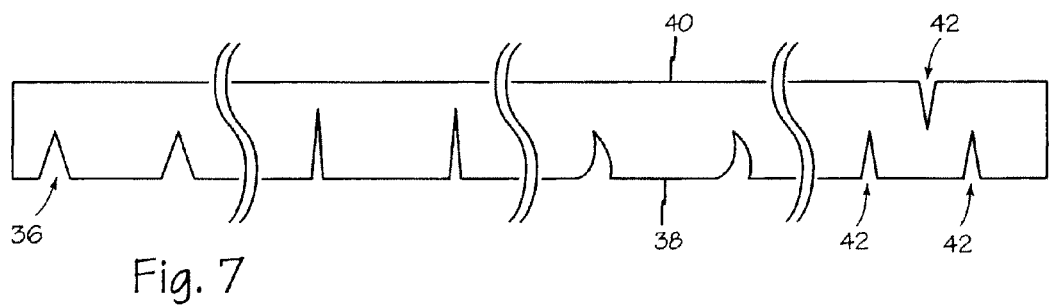

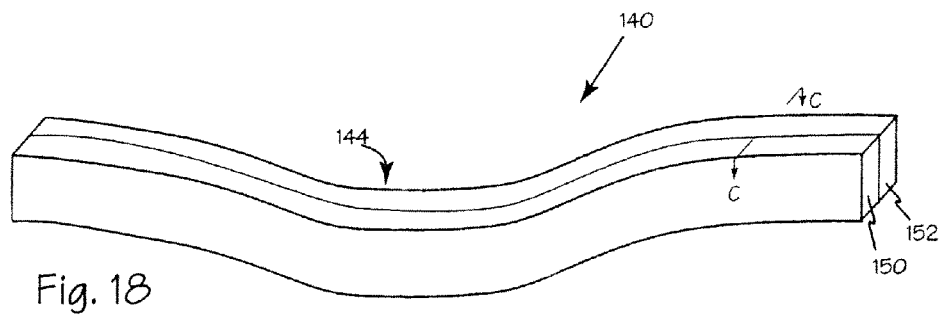
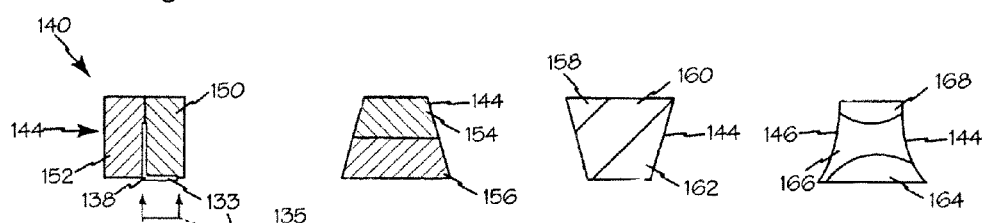
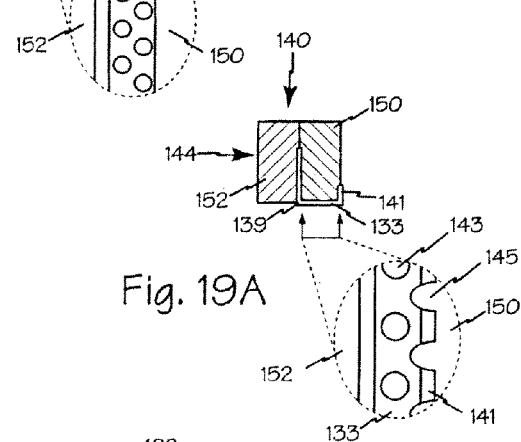
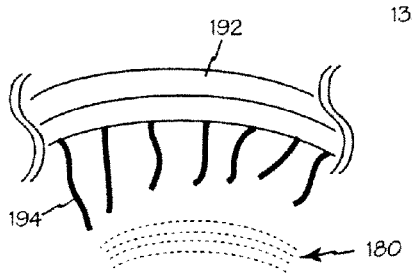
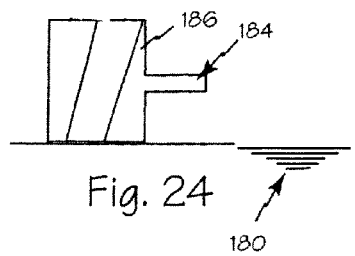

WOUND SHIELD WITH ENCLOSED VACUUM SPACE

CROSS-REFERENCE TO RELATED APPLICATIONS

This application is a continuation, under 35 U.S.C. §120, of U.S. patent application Ser. No. 11/303,155, filed on Dec. 15, 2005 now U.S. Pat. No. 7,601,129 and entitled "Wound Shield and Warming Apparatus and Method," the entire contents of which are incorporated by reference herein.

FIELD OF THE INVENTIONS

The inventions described below relate the field of wound care management.

BACKGROUND OF THE INVENTIONS

Wounds occur when the integrity of any tissue is compromised, affecting one or more layers of skin or underlying tissue. Wounds may be caused by an act, surgical procedure, an infectious disease or an underlying condition. Examples of open wounds include punctures, abrasions, cuts, lacerations and burns. Chronic wounds are also common ailments and include pressure ulcers, diabetic ulcers, arterial ulcers, venous ulcers or combination of all the above. Despite much progress made in the wound care industry, an efficient and effective method and apparatus for protecting the wound from injurious contacts is not readily available.

Injurious contacts with foreign objects may be caused from various sources, ranging from brushing of clothing or bed sheets to fresh, uncovered wounds to adherence of wound dressing to the wound. The latter issue, referred to here as the sticking issue, leads to deleterious consequences for the patient. This problem is particularly exacerbated when wounds are left unattended for a substantial period. It is reported that in certain circumstances patients are administered morphine to withstand the pain caused form dressing removal, especially with wounds having a large surface area. Equally important, tearing of skin graft, newly formed cells or scab adhered to dressing disrupts the healing process.

Wounds are generally covered to prevent contamination and resulting infection. Wounds may also be covered for other reasons, including retaining moisture and absorption of exudate. Wound covering has traditionally consisted of application of dressings that are in direct contact with the wound. When directly applied on the wound, dressings adhere and mechanically anchor to wound surface, which may include diffused wound fluid, skin graft, new epidermal cells forming over the wound or the scabby covering of the wound.

The sticking issue has traditionally been addressed by soaking the wound and the dressing adhering to it in water for sometime to soften the scab and make removal easier. Another method is the application of antibiotic ointments, such as polymyxin B sulfate or bacitracin, to keep the bandage from sticking to the wound. These methods, however, have not sufficiently addressed the sticking issue. As can be appreciated by health care professionals, soaking in water or application of ointments are not always practicable or recommended.

To better address the sticking issue the medical industry has developed "non-stick" dressings such as Telfa® and Xeroform® and other dressings such as hydrocolloids, alginates, hydrofilms, etc. Non-stick, however, is a relative term. Non-stick dressings merely stick less than their traditional counterparts, e.g., cotton gauze. Another problem with these dressings is that their cost is prohibitive for use on wounds requiring constant change of dressing.

"Non-contact" dressings have also been invented to address the sticking issue. These dressings are primarily designed in the shape of an inverted cup or a raised bandage. The general idea is that the space within the cup or raised bandage covers the wound, but does not come in contact with it.

Similar to the traditional and "non-stick" dressings described above, "non-contact" dressings also fail to efficiently and effectively protect the wound from contact, including addressing the sticking issue. First, they cannot be sufficiently deformed for the specific contours of different wounds, such as a narrow, long laceration. Second, they are designed in specific sizes that are not necessarily the desirable size for the wound.

Aside from their size limitation and lack of deformability, the prior art "non-contact" dressings have other drawbacks. Their complicated design makes their costs a prohibitive factor and application difficult. Moreover, whether several dressing sizes bundled together, or more than one dressing is in use, the prior art non-contact dressings are unable to address wounds on body segments with small surface areas. For example, using a large square, oval or circular bandage to cover a large, narrow and oddly shaped laceration on the forearm or shin is impractical. The same is true for the face and neck regions. Similarly, due to their specific shape and size, the non-contact dressings of prior art are not able to address wounds located in joints, such as elbows or knees.

What is needed is a method and apparatus for dressing wounds or other suitable injuries that is conformable, adjustable and flexible to prevent contact with the surface of the wound and improve the environment immediately adjacent the wound.

SUMMARY

A wound shield may include a conformable frame to circumscribe a wound. Any suitable dressing may be secured over the conformable frame, the conformable frame providing separation between the wound and the dressing. The wound frame may provide pressure relief around a wound or pressure sore to permit healing, allow compression for venous ulcers, retain moisture within the wound environment, absorb exudate, relieve pain and trauma associated with dressing removal, allow debridement and application of topical medications and or other compounds or chemicals, accelerate healing and facilitate monitoring of wounds. A conformable frame may be composed of one or more layers of any suitable material and may include adhesive on one or more surfaces to secure the frame to the wound site, to secure the frame to itself and or any suitable closure element and or to secure the dressing to the conformable frame. A wound shield may be used for humans or any suitable animal.

A wound shield according to the present disclosure may be a simple, versatile, inexpensive and readily applicable apparatus and method for wound protection. It may include a conformable wound-protecting frame that may conform to the specific contour and size of any wound and may be used with any suitable dressing. A wound shield prevents foreign objects such as clothing, dressings and other such items from contacting the wound. Cotton gauze or other suitable dressing may be placed on or engage a wound protecting frame to completely protect the wound from harmful contact with any object. Alternatively, special covers, seals, and or lids may be placed on the wound shield to control moisture, simplify wound monitoring and debridement and application of medications.

A wound shield according to the present disclosure may adhere to skin surrounding a wound via adhesive applied to a surface of the wound-protecting frame to engage the skin. Medical grade, hypoallergenic adhesives are preferred, although any suitable adhesive may be used such as rubber-based, acrylic, vinyl ether and suitable pressure-sensitive adhesives. For their obvious advantages, adhesives that adhere to body hair less than their conventional counterparts are preferred. Adhesives may also be added to one or more surfaces of a wound-protecting frame not in contact with skin to engage any suitable dressing, cover, lid or any other suitable closure. Alternatively, no adhesive is used with the wound shield, and the wound shield is retained in place by the pressure applied from the dressing wrapped around the wound.

A conformable wound shield frame may be provided in any suitable dispenser configuration. For example, the conformable frame may be wound around a reel and placed in a dispenser that can be efficiently stored. When needed, the conformable frame may be fed out of the dispenser, and cut to desired lengths. Alternatively, the wound-protecting frame may be supplied in a sheet form and cut to the desired length and width. Moreover, the conformable frame may be pre-packaged in several long strips with various or equal widths that may be cut to desirable lengths In use, a conformable frame is placed around a wound, creating a boundary and providing a plane separate from the plane of the wound to support the dressing. The conformable frame may be used with any suitable closure to engage the ends of the conformable frame and encircle a wound.

A wound shield according to the present disclosure may be fully deformable to conform to specific contours of any wound located on any surface of a body. It may be cut to a desirable length to enclose all or any portion of the perimeter of any wound, regardless of shape and size. In addition, the conformable frame may be made of inexpensive and yet effective material.

Any suitable dressing may be used in conjunction with the conformable frame, and may range from inexpensive, commonly used cotton gauze to more costly and sophisticated dressings, including for example, those constructed from transparent and or multi-layered material with qualities such as exudate absorption, bacteria impermeability and controlled air and or moisture permeability. Health care professionals may mix and match various dressings without restriction to complex and/or costly non-contact dressings.

A wound shield according to the present disclosure has sufficient rigidity to prevent injurious contacts to the wound, including those caused by dressing adhering to the wound surface. The conformable frame prevents contact to wounds regardless of their size or location with any suitable dressing.

A wound shield according to the present disclosure may be used for swift and effective wound debridement using any suitable technique. For example, a wound shield may be used to create a controlled space adjacent a wound for biological debridement, use of maggots or other suitable techniques. Alternatively, mechanical and or chemical debridement may also be effected within the controlled space. Surgical debridement may also be performed without removing the conformable frame from around the wound. The wound shield minimizes wound and peri-wound disturbance by avoiding repetitive dressing removals with the associated wound surface disturbance.

A wound shield including a conformable frame to circumscribe a wound and warm water circulating system to maintain a warm environment. Any suitable dressing may be secured over the conformable frame providing separation between the wound and the dressing. The wound frame may provide pressure relief around a wound or pressure sore to permit healing. A conformable frame may be composed of one or more layers of any suitable material and may include adhesive on one or more surfaces to secure the frame to the wound site and or to secure the dressing to the conformable frame.

BRIEF DESCRIPTION OF THE DRAWINGS

FIG. 1 is a perspective view of a conformable frame according to the present disclosure.

FIG. 2 is a cross section of the conformable frame of FIG. 1 taken along A-A.

FIG. 3 is an alternate cross section of the conformable frame of FIG. 1.

FIG. 4 is another alternate cross section of the conformable frame of FIG. 1.

FIG. 5 is a still alternate cross section of the conformable frame of FIG. 1.

FIG. 6 is a perspective view of an alternate conformable frame according to the present disclosure.

FIG. 7 is a top view of a conformable frame similar to FIG. 6 illustrating alternative configurations.

FIG. 18 is a perspective view of an alternate deformable wound frame according to the present disclosure.

FIG. 19 is a cross section of the conformable frame of FIG. 18 taken along C-C.

FIG. 19A is a cross section of the conformable frame of FIG. 18 taken along C-C with an alternate scaffold.

FIG. 20 is an alternate cross section of the conformable frame of FIG. 18.

FIG. 21 is another alternate cross section of the conformable frame of FIG. 18.

FIG. 22 is yet another alternate cross section of the conformable frame of FIG. 18.

FIG. 23 is an alternate cross section of the conformable frame of FIG. 18 with a wicking element.

FIG. 24 is another alternate cross section of the conformable frame of FIG. 23.

FIG. 25 is a perspective view of an alternate conformable frame according to the present disclosure.

DETAILED DESCRIPTION OF THE INVENTIONS

Figure 8:
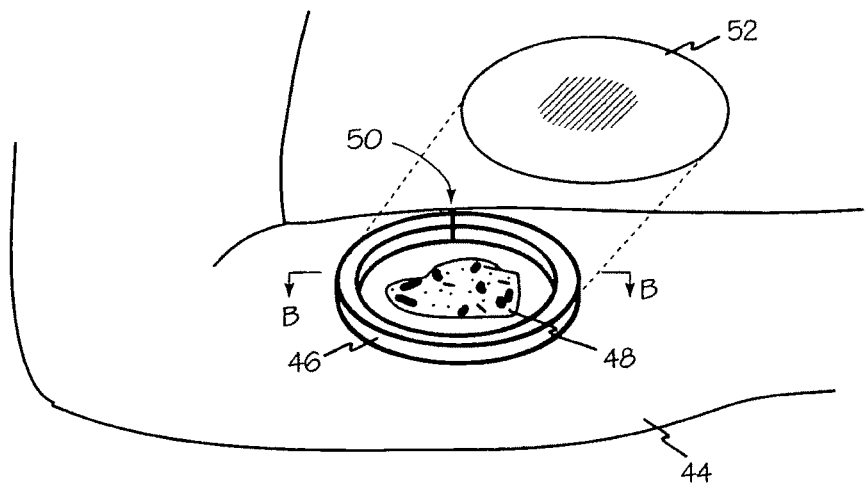
FIG. 8 is a perspective view of a conformable frame surrounding a small wound on the forearm.

Referring to FIG. 1 and FIG. 2, conformable frame 10 provides perimeter protection for a wound and may conform to specific contours of the wound site. Conformable frame 10 includes exterior side 14 facing away from the wound and interior side 16 facing the wound, superficial surface 12 for engaging dressings and cutaneous surface 18 in contact with the patient's skin, or any other dressing or apparatus in contact with the patient's skin. Any suitable adhesive may be applied to cutaneous surface 18 and or superficial surface 12 such as adhesive 28 and 22 respectively. Adhesive layers 22 and 28 may also be covered by a strip or a film, such as film 24 and 26 respectively, that can be peeled off at the time of use. Adhesive 28 secures conformable frame 10 to skin surrounding a wound, or in some applications, to a dressing or apparatus that is in contact with the patient's skin. When applied to superficial surface 12, adhesive layer 22 may engage a dressing or other suitable cover to conformable frame 10.

In use, conformable frame 10 includes a first end 13 and a second end 15. When positioned around a wound, first end 13 and second end 15 may be engaged to completely circumscribe the wound as shown in FIG. 8. An adhesive or other suitable material may be applied to first end 13 and or second end 15 to secure the engagement of first end 13 and second end 15. Conformable frame 10 may have any suitable cross-section as shown in FIG. 2 including height 30 and width 32. The size of a wound site to be circumscribed may require height 30 and width 32 to be available in different dimensions. Larger wounds may have a dressing sag and inadvertently contact the wound. First end 13 and or second end 15 may be cut, preshaped or scored such that first end 13 and or second end 15 are not perpendicular to the interior and exterior surfaces, or the superficial and cutaneous surfaces. The angle between the end surface and the side of the conformable frame may be selected to optimize the curvature of the conformable frame, or to increase the mating surface areas of the ends.

Conformable frame 10 may be constructed from any suitable material capable of deformation in the X and or Y and or Z-axes. Silicone is one example of such material, as it is both rigid and deformable. Polymers such as polypropylene, polyethylene and polyurethane may also be used to form a deformable, and yet rigid wound protector. Depending on its specific use, additional features of a wound shield may include impermeability or controlled permeability to water, bacteria and air, and absorption of fluids exuding from the wound bed. A wound shield according to the present disclosure may also include a selectable moisture vapor transmission rate (MVTR). Polyurethane foam may be used to form a wound-protecting frame for its ability to absorb exudates.

Referring now to FIGS. 3-5, alternative cross sections may be used. Any suitable cross section may be used.

Referring now to FIG. 6, alternatively, a conformable frame such as conformable frame 34 may also include a plurality of grooves, cuts or slots such as grooves 36, positioned in either the wound or exterior side such as exterior side 38. Grooves 36 may increase flexibility of conformable frame 34 when constructed of material that may not have sufficient inherent flexibility to allow appropriate conformability. Grooves 36 may be cut or otherwise formed in conformable frame 34 using any suitable technique.

Referring now to FIG. 7, alternate configurations of grooves 36 are illustrated for example. Any suitable geometry may be used for grooves 36. Grooves or slots or cuts such as cuts 42 may also be combined in exterior side 38 as well as wound side 40 for increased flexibility.

Figure 9:
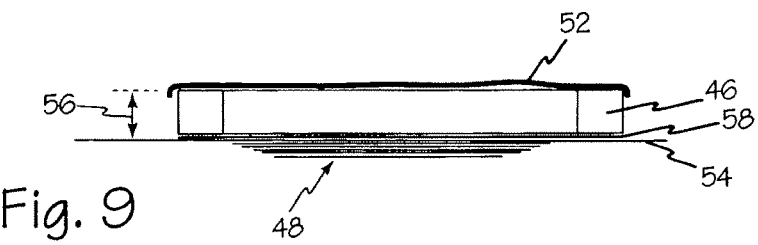
FIG. 9 is a cross section of the conformable frame and dressing on the wound of FIG. 8.

Referring now to FIG. 8 and FIG. 9, conformable frame 46 may be superficially applied to any injured surface of a patient such as forearm 44 using adhesive 58. Conformable frame 46 circumscribes wound 48. First end 13 and second end 15 engage at plane 50. When dressing 52 is used to promote healing of wound 48, conformable frame 46 prevents dressing 52 from contacting wound 48 by creating a separation 56 between dressing 52 and wound plane or skin surface 54. Separation 56 is controlled by height 30 of the conformable frame.

As briefly described above, dressing 52 may be any suitable dressing. Dressing 52 may also include adhesive along its perimeter or longitudinal and/or its transverse lengths, so to facilitate its adherence to skin surrounding conformable frame 46. Alternatively, dressing 52 may be wrapped around the arm or other body parts on which wound 48 is situated, or dressing 52 may be sized or cut to size to engage only conformable frame 46. Dressings such as dressing 52 may have any suitable MVTR parameters.

Figure 10:
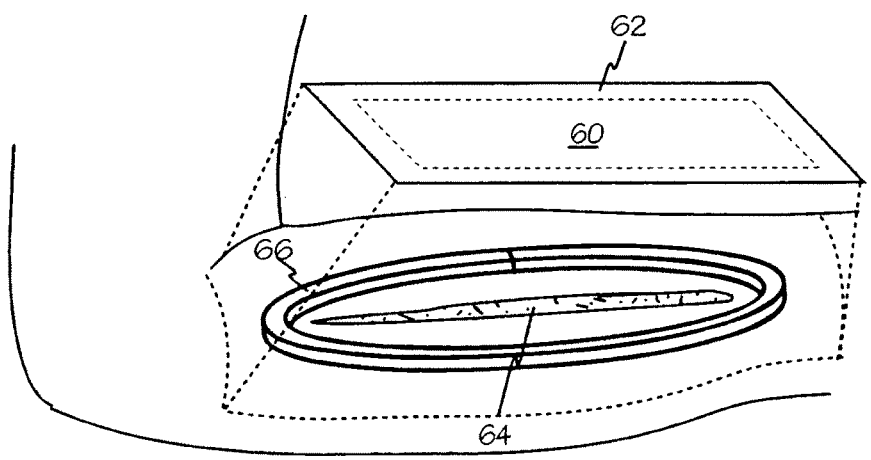
FIG. 10 is a perspective view of a conformable frame surrounding a long, oddly shaped laceration on the forearm.

Referring now to FIG. 10, dressing 60 may be used to secure conformable frame 66 around wound 64, which is a long, narrow, oddly shaped laceration. Adhesive may be included around perimeter 62 of dressing 60. One or more dressing such as dressing 60 may be used. Dressing 60 may be applied along the length, width, or in tandem with another dressing 60 or other dressings to protect wound 64.

Figure 11:
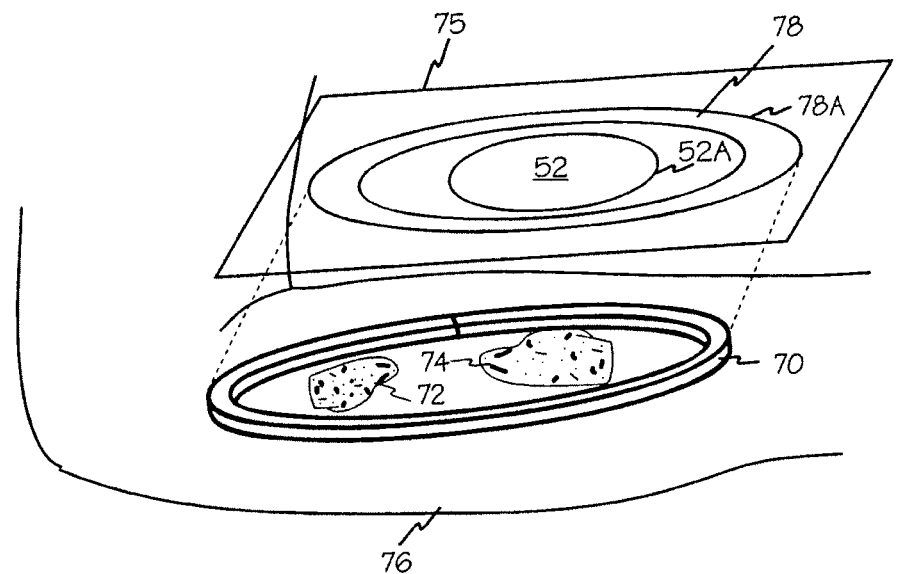
FIG. 11 is a perspective view of a conformable wound frame surrounding two proximately located wounds on the forearm.

Referring now to FIG. 11, conformable frame 70 may be used to protect one or more proximately located wounds such as wounds 72 and 74 on forearm 76. Dressing 78 may be separated from scored dressing sheet 75 which may have one or more dressings scored into sheet 75. Dressings such as dressing 52 or dressing 78 may be separated from sheet 75 along scoring 52A or 78A respectively. Any size or number of dressings may be pre-scored into a dressing sheet such as sheet 75.

Figure 12:
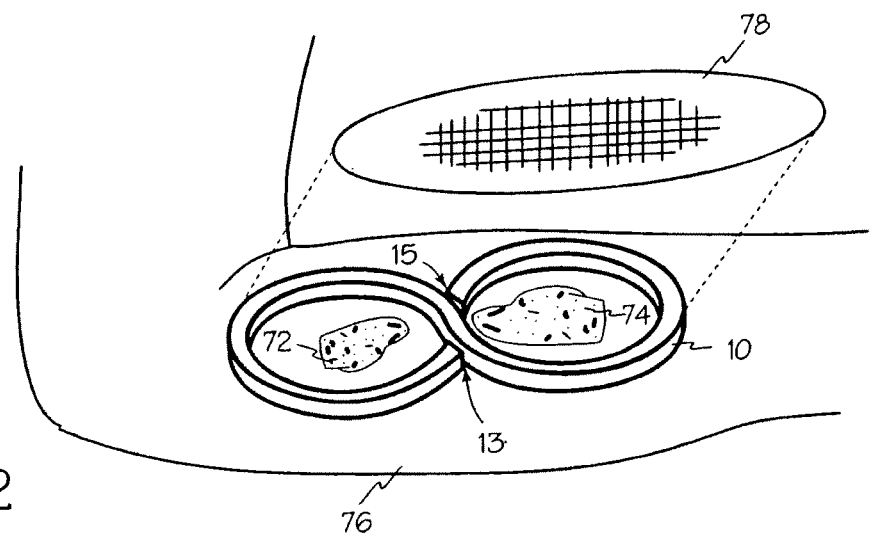
FIG. 12 is a perspective view of an alternate configuration of a conformable wound frame surrounding two proximately located wounds on the forearm.

In an alternate configuration shown in FIG. 12 the connection of first end 13 and second end 15 is transected by conformable frame 10. The use of a figure-8 shape provides dressing and pressure support between wounds 72 and 74. To prevent exudate from flowing away from wounds 72 and 74 first end 13 and second end 15 may contact or otherwise engage side 14 and side 16 respectively.

A conformable frame according to the present disclosure may not always completely circumscribe a wound. For wounds positioned in awkward body locations, such as the elbow and knee or for any other reason, a conformable frame may be cut into two or more suitable lengths or frame elements. The frame elements may be positioned around the wound as discussed above. Such manipulation may allow positioning of a dressing without contacting the wound.

In certain circumstances health care professionals may recommend the airing of the wound, i.e., not covering the wound with any dressing. As such, a conformable frame according to the present disclosure may be used to simply protect the wound from physical contact with other foreign objects, such as clothing or bed sheets. This configuration may also be suitable for treatment of pressure or abrasion sores from long term immobility. Conformable frame may be used to surround such sores and relieve the local pressure and permit the sores to heal.

For patients allergic to medically approved adhesives, the conformable frame may be provided without adhesive or, alternatively, with adhesive only on surface 12. In such circumstances, conformable frame 10 must be secured to the wound site with sufficient and appropriate pressure to engage conformable frame 10 with the wound site.

For wound configurations such as illustrated in FIG. 11, particularly large wounds, structurally weak dressings or high pressure wound or sore sites it may be necessary to provide additional support within the perimeter of a conformable frame to support the selected dressing or relieve external pressure.

Figure 13:
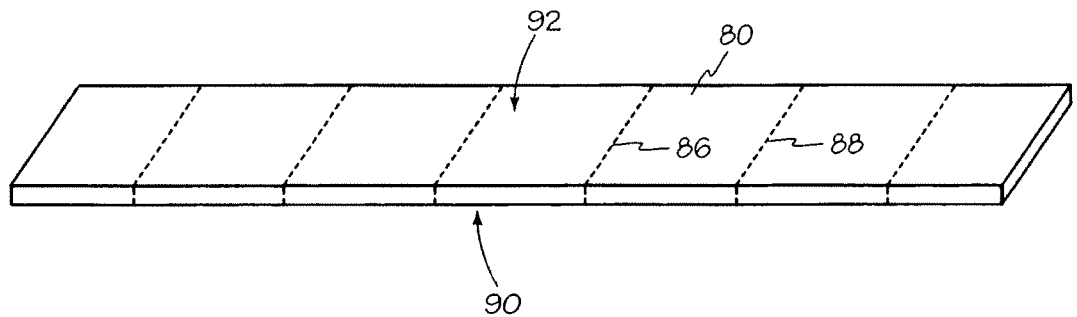
FIG. 13 is a perspective view of a support or bridge member according to the present disclosure.
Figure 15:
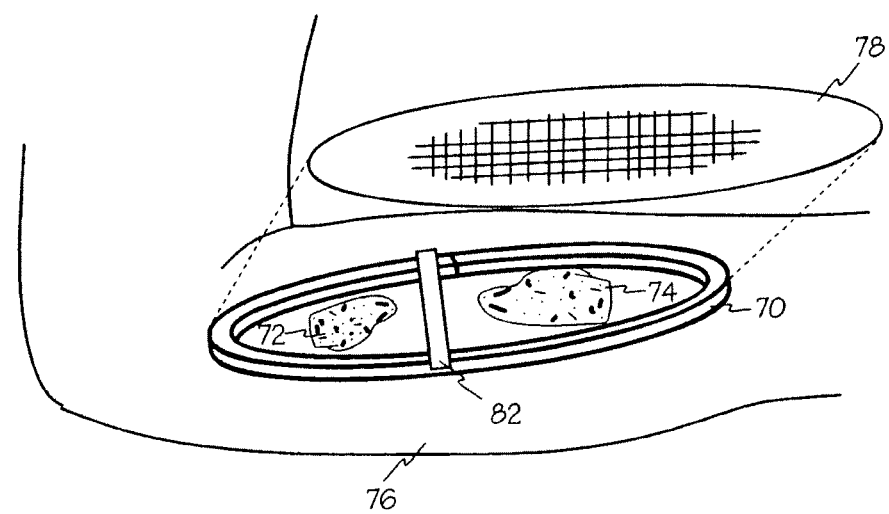
FIG. 15 is a perspective view of a conformable wound frame surrounding two proximately located wounds on the forearm.

Referring now to FIG. 13, one or more bridge members such as bridge member 80 may be used with the conformable frame of the present disclosure to provide additional wound protection. A bridge member may be used with wounds having large surface area or with dressings having little structural strength, or in situations where pressure may be applied to the center of the wound area. Positioning of one or more bridge members such as bridge 82 on conformable frame 70, as depicted in FIG. 15, may prevent dressing 78 from sinking and touching wounds 72 or 74.

A bridge member can have any suitable shape including straight or curved edges, ends or separations. A bridge may also be constructed from inexpensive medical grade rigid plastic polymers, metal or wood particularly conditioned for medical use. Such material may be structurally adapted to allow breakage or separation along segment lines such as lines 86 and 88.

Medical grade adhesive may also be applied to second surface 90 which will come in contact with the conformable frame. A thin layer of film or strip removable at time of use may cover the adhesive as discussed above with respect to the conformable frame. Alternatively, bridge member 80 may have adhesive on both second side 90 and first side 92 to adhere not only to the conformable frame, but also to the dressing.

Figure 14:
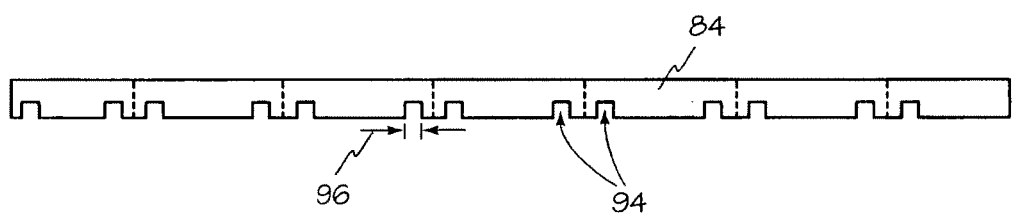
FIG. 14 is a side view of an alternate support or bridge member according to the present disclosure.

Referring now to FIG. 14, alternate bridge member 84 includes a plurality of slots 94. Each slot or opening such as slot 94 may have any suitable shape and dimension providing that width 96 is sized to permit engagement of a suitable conformable frame in the slot.

Figure 16:
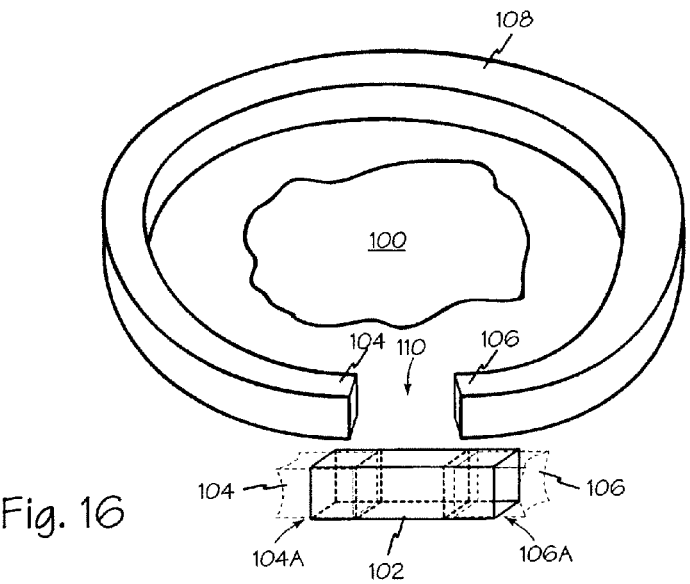
FIG. 16 is a perspective view of a connector used in conjunction with a conformable member.

Referring now to FIG. 16, a connector such as connector 102 may be used to join ends 104 and 106 of conformable frame 108 and provide complete closure around a wound such as wound 100. Any suitable connector such as connector 102 may be used in circumstances where it is desirable not to apply any adhesive to surfaces of conformable frame 108, or where repetitive engagement and disengagement of first and second ends 104 and 106 make adhesive impractical. Lack of adhesive provides the opportunity for first end 104 and second end 106 to move away from one another and create an opening 110. As can be appreciated, exudate from wound 100, if any, may diffuse away from wound 100 through opening 110 and onto other body surfaces.

Connector 102 may be used to close opening 110 by indirectly connecting first end 104 and second end 106. Connector member 102 may be hollow, and may be constructed from any suitable material, including those used for construction of conformable frames. Engagement receptacles 104A and 106A may be slightly larger than the dimensions of first end 104 and second end 106 respectively. This permits conformable frame 108 to be inserted into connector member 102. Receptacles 104A and 106A should provide secure engagement to first end 104 and second end 106 respectively. Any other suitable configuration may also be used. Connectors such as connector 102 may also be used to connect two or more conformable frames.

Figure 17:
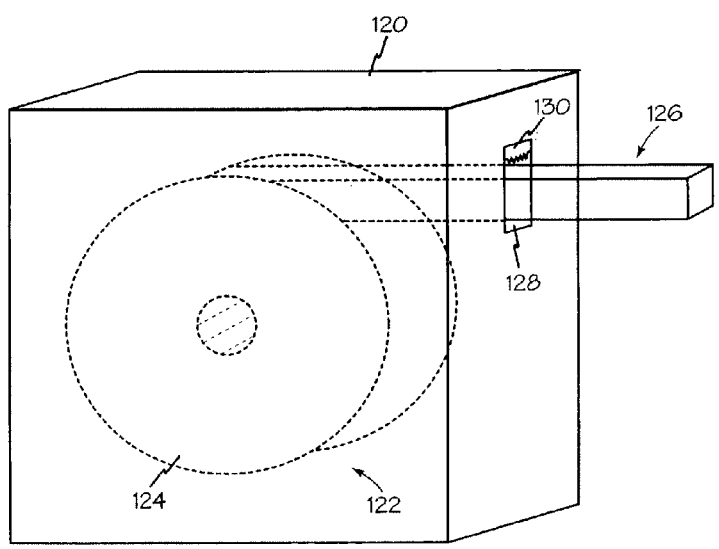
FIG. 17 is a perspective view of a dispenser according to the present disclosure.

Referring now to FIG. 17, conformable frames such as conformable frame 10, conformable frame 34 and others may be stored and dispensed from any suitable dispenser. For example, dispenser 120 may contain one or more coils such as coil 122 wound around a reel or hub 124. Segment 126 may be a portion of conformable frame from coil 122 that is withdrawn through outlet 128. Segment 126 may be pulled out from outlet 128 and cut to a desired length with scissors, or via one or more blades 130 positioned adjacent outlet 128.

Alternatively, a dispenser may be sterilized, and or may have several outlets allowing it to contain several coils containing conformable frames having different dimensions and or characteristics. The number of coils or outlets contained in a dispenser are examples provided for discussion purposes only and should not be viewed as a limitation.

Figure 17A:
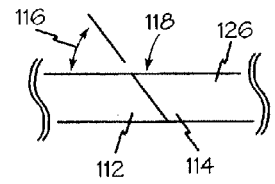
FIGS. 17A and 17B are top views of conformable frame joints formed using the dispenser of FIG. 17.

Referring now to FIG. 17A, conformable frame segment 126 is separated from dispenser 120 forming first end 112 and second end 114. During separation of segment 126 first end 112 and second end 114 were cut, scored or otherwise separated to form angle 116 with exterior side 118. Decreasing angle 116 increases the surface of the first and second end enabling greater engagement. A first end and second end may be cut to similar angled, complementary angles or different angles. Alternatively, first end 112 and second end 114 may be precut or otherwise prepared in standard lengths with assorted end profiles.

Figure 17B:
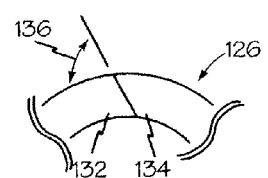

Referring now to FIG. 17B, first end 132 and second end 134 may be cut at a different angles 136 to simplify joining the first and second ends and form curves or shapes having small radii.

In use, a second conformable frame may be positioned on the superficial surface of a first conformable frame. This configuration may be used in situations where a greater protective height around a wound is preferable. A stacked assembly may include more than two conformable frames.

Referring now to FIG. 18, conformable frame 140 may have many different cross sectional dimensions as well as constituent configurations. Conformable frames as discussed above may adopt any suitable geometry. For some applications it may be useful for a conformable frame to be composed of two or more internal layers such as layers 150 and 152 illustrated in FIG. 19. For example, layer 150 may be absorbent, or may include any suitable antibiotic such as for example silver metal and or its salts. Layer 152 may be made from any suitable material.

In some situations it may be preferable to change one or more layers closest to a wound when the layer or layers become saturated or otherwise unsuitable to remain close to the wound. Layer 150 may also be removable to permit changing one or more layers. A scaffold or other suitable apparatus such as scaffold 138 may be secured to exterior layer 152. Internal layer 150 may be secured or otherwise engaged to either or both layer 152 and scaffold 138.

Alternatively, internal layer 150 may be positioned using scaffold 138. Securing layer 150 to layer 152 and scaffold 138 using water soluble adhesive would simplify removal of layer 150 and may also serve to identify a saturated layer as it separates from the structural layer and the scaffold. If layer 150 needed to be changed, any dressing or lid applied over conformable frame 140 may be disengaged. Layer 150 may be removed and a replacement layer may be inserted using scaffold 138 as a guide and engagement mechanism.

Referring now to FIG. 19A, an alternate scaffold 139 may include lip 141 to frictionally engage layer 150 without the use of adhesive or other bonding agent. Scaffold 138 and or scaffold 139 may also include holes or other suitable openings such as holes 135 and 143 and openings 145 in shelf 133 and or lip 141 as illustrated in the associated close-up bottom views. Lip 141 may also permit usage and of any suitable absorbent material in a non-contact position relative to the wound. The absorbent material may be frictionally engaged by lip 141 and supported by scaffold 139.

Some materials may have directional characteristics, and when combined in multiple layers may offer unique benefits. Many additional characteristics may also be useful, for example, layer 156 of FIG. 20 may be absorbent to absorb and retain exudate from the wound, and layer 154 may be formed of a material providing dimensional stability or structural integrity.

Similarly, referring to FIG. 22, layer 164 may be absorbent and layer 166 may provide structural integrity and layer 166 may enclose layer 164 to prevent exudates from wound side 144 transiting conformable frame 140 and exiting through exterior side 146. Any suitable material may be selected for each layer. Layer 168 may be any suitable material.

Referring now to FIG. 21, layers 158, 160 and 162 may also provide one or more diagnostic indicators such as for example, ph level, temperature, moisture level, $O^2$ levels or any other suitable parameter. The state of the parameter may be indicated by one or more color states of one or more layers.

Referring now to FIG. 23, conformable frame 170 may include one or more internal layers such as layers 172, 174 and 176 and one or more absorbent appendages such as arm 178. Arm 178 and layer 176 may be composed of any suitable material for absorbing exudates from wound 180. The physical geometry of arm 178 may vary for varying applications. For example, arm 184 shown in FIG. 24 provides vertical relief from wound 180.

Alternatively as illustrated in FIG. 25, flexible absorbent appendages may also be secured to a conformable frame such as conformable frame 192. Absorbent appendages 194 may be provided to absorb exudate from wound 180. Any suitable material or combination of materials may be used as appendages 194 such as for example natural fibers such as cotton or any suitable man-made fiber. Any other suitable configuration may also be employed such as enclosing one or more cotton balls or gauze within the space enclosed by a conformable frame and a covering dressing.

Figure 26:
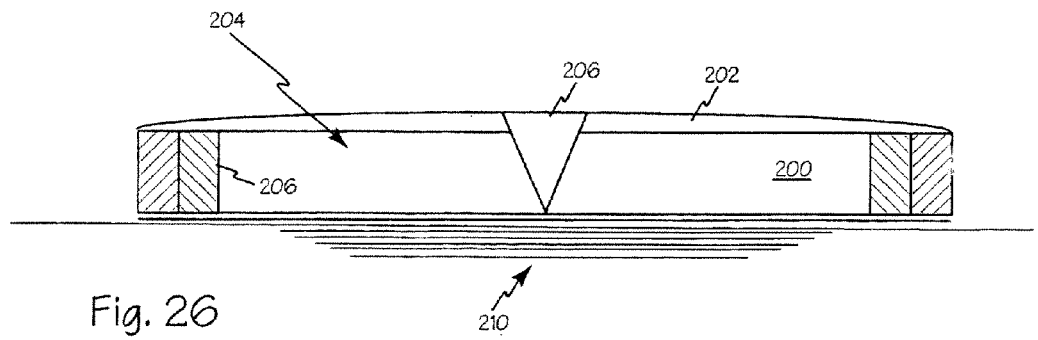
FIG. 26 is a cross section of an alternate conformable frame and lid configuration.

Referring now to FIG. 26, conformable frame 200 may also be used with a cover or lid 202 to provide a controlled environment in enclosed space 204 adjacent a wound site. Lid 202 may be removably engaged to conformable frame 200 using any suitable technique such as frictional or adhesive engagement. Lid 202 may be formed of any suitable material or combination of materials such as a structural grid layer with one or more laminate layers to obtain suitable performance and moisture transmission/retention.

Alternatively, lid 202 may also include one or more absorptive elements such as cone 206 for removing moisture or exudate from wounds such as wound 210. Absorptive elements may have any suitable shape or dimension and may be formed of any suitable material. For example, cone 206 may be formed of material that is selectively absorbent to remove exudate and unwanted fluids.

Figure 27:
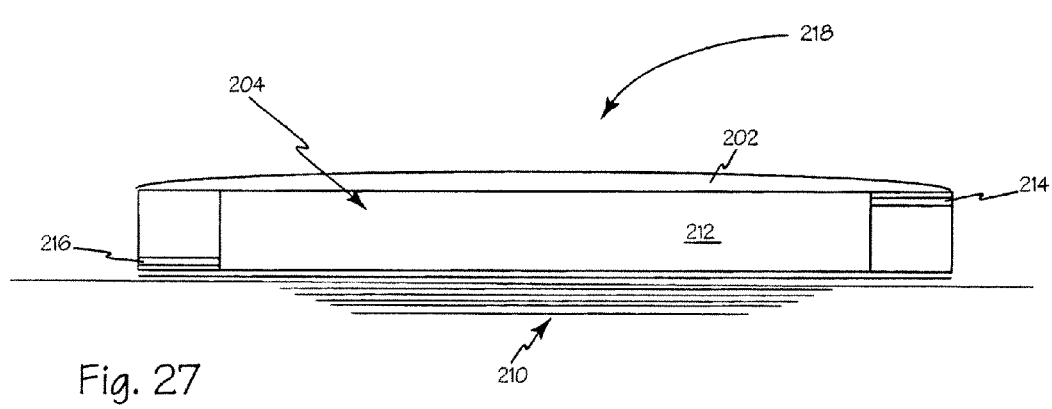
FIG. 27 is a cross section of another alternate conformable frame and lid configuration.

Enclosed space 204 may be further controlled as illustrated in FIG. 27. Conformable frame 212 may include one or more access ports such as inlet port 214 and outlet port 216. Use of access ports permits irrigation, treatment, and or debridement of wound 210 without removing wound protection shield 218. Fluid or other material may be introduced into enclosed space 204 through inlet port 214. In the case of used fluid or exudate, removal may be accomplished using outlet port 216. Access ports such as inlet port 214 and outlet port 216 may be reclosable to secure enclosed space 204. Alternatively, conformable frame 212 may be formed of material that permits a syringe to be inserted through the conformable frame for insertion of material or to remove material. Access ports may also be formed in the cover or lid 202.

Figure 28:
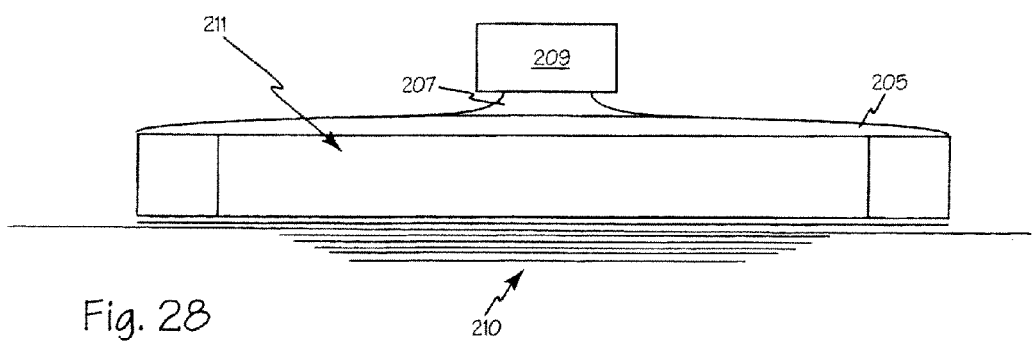
FIG. 28 is a cross section of a conformable frame with a vacuum lid configuration.

Referring now to FIG. 28 enclosed vacuum space 211 may be created and maintained by the use of a suitable cover or lid such as vacuum lid 205. A partial or complete vacuum may be created in space 211 by vacuum device 209 through adapter 207 or through a conformable frame such as conformable frame 212 using inlet port 214 or outlet port 216. Using a conformable frame and specifically adapted lid such as lid 205 may permit a vacuum device such as vacuum device 209 to be located on lid 205 without creating unsatisfactory pressure on or adjacent wound 210. Lid 205 may require an adapter such as adapter 207 or lid 205 may be specifically formed to adapt to a vacuum device or connector to a vacuum device to create a full or partial vacuum within space 211.

Figure 29:
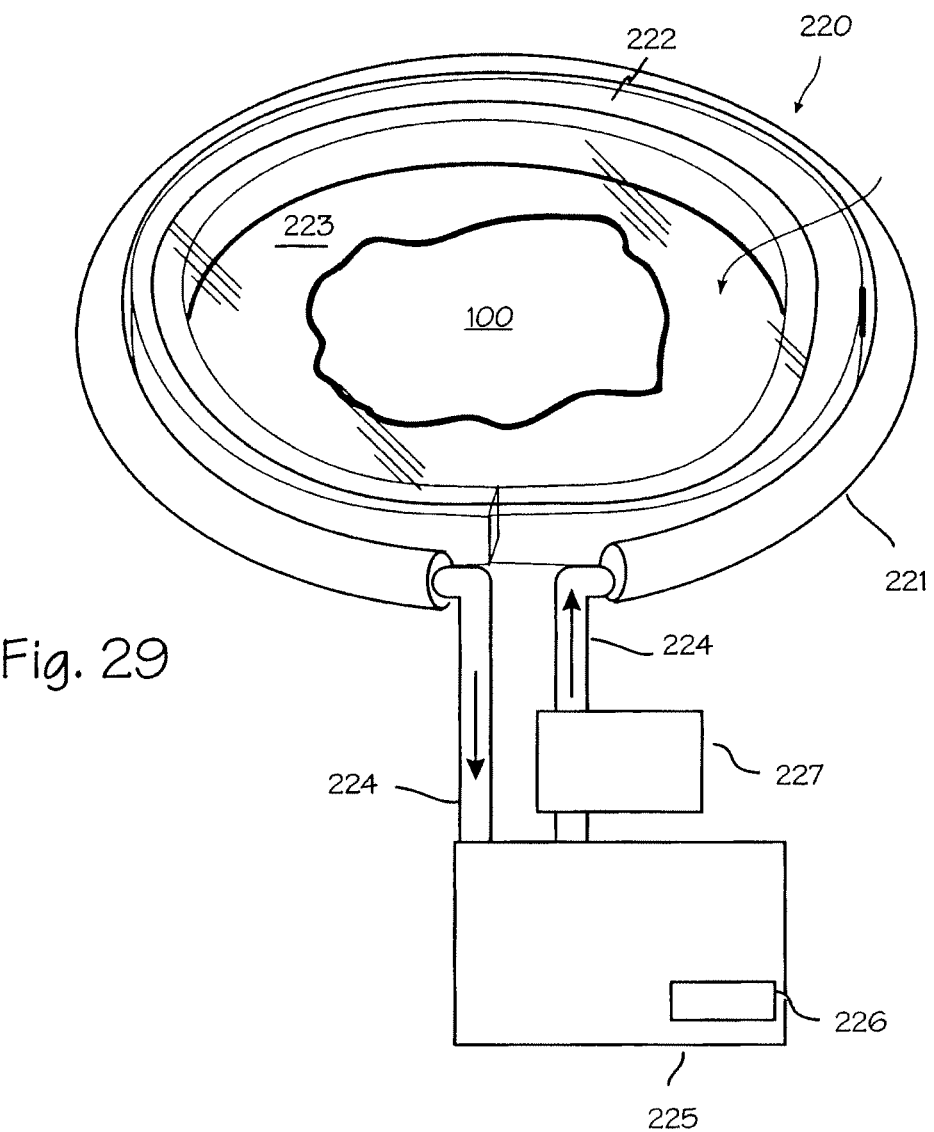
FIG. 29 illustrates a device for isolating a wound and providing heat to the wound to encourage healing.

FIG. 29 illustrates the wound isolation and warming device 220, including the conformable tube 221, inner absorbent ring or strip 222 and breathable vapor barrier 223. The tube and absorbent strip are provided with any suitable adhesive on the cutaneous surfaces of the tubing, the strip, or both, to secure the device to the skin of a patient. The conformable tubing is made of polyethylene or other thermally conductive material, and is preferably conformable to the extent that it may either be bent and formed as necessary to conform to the contours of a patient's body, though it may be supplied in straight lengths or in coils. The device also includes water supply and return conduits 224, and a warm water source 225 comprising a water reservoir, heater 226 (or any other suitable heating means), pump 227, and appropriate thermostats, heating regulators and flow regulators. Pulsatile flow can be provided with roller pump or centrifugal pulsatile flow pump. The heater and thermostat are preferably operable to maintain water temperature at a therapeutic temperature of about 105° F. (about 40° C.), but may be operated to maintain higher or lower temperatures as medically indicated. The device is illustrated in place surrounding wound 100 on the skin of a patient.

Figure 30:
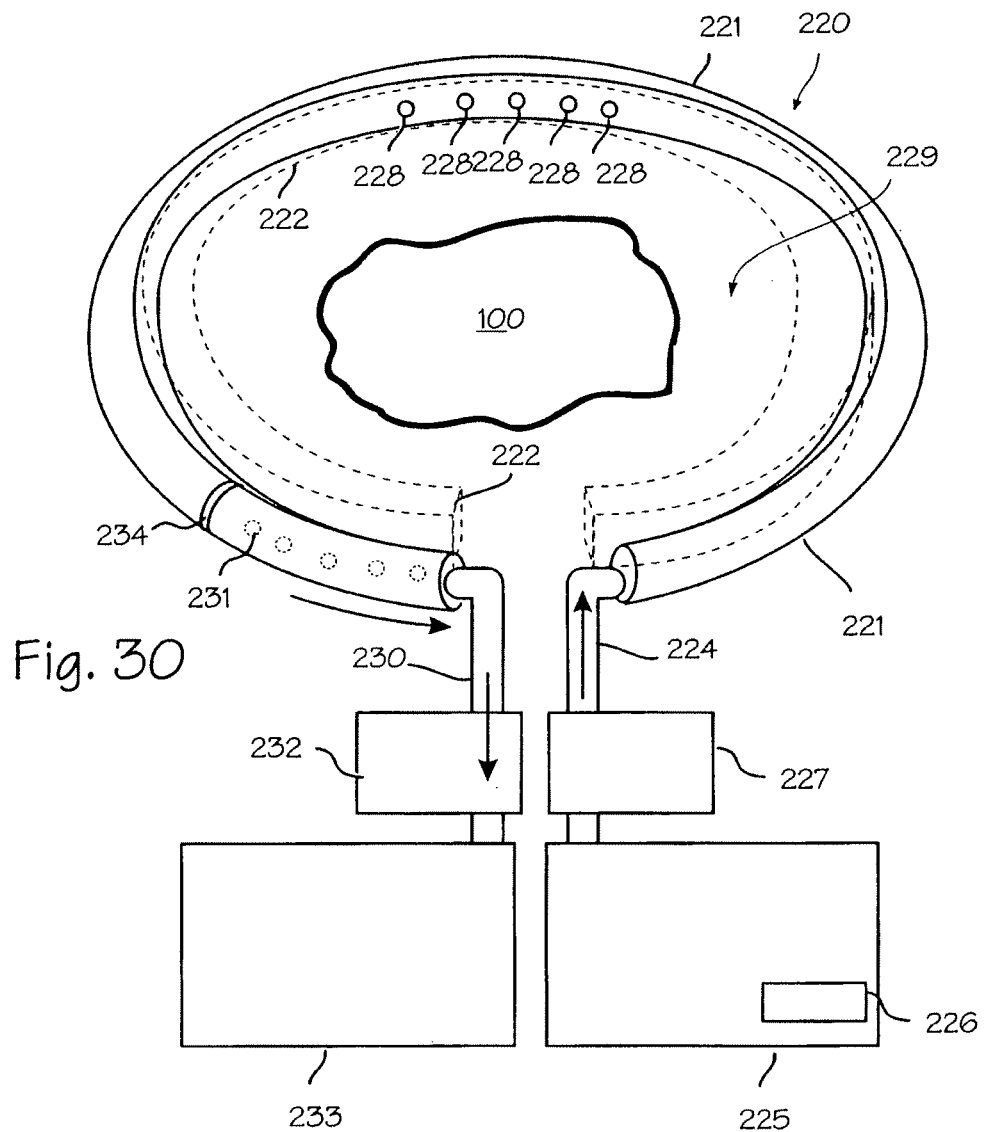
FIG. 30 illustrates the device of FIG. 29 modified to provide fluid flow over the wound to encourage healing.

The device may be modified as shown in FIG. 30, in which the tube 221 in the vicinity of the wound is perforated, such that apertures 228 distributed along the inner wall of tubing 221 and any intervening portion of conformable frame 222 direct water into the interior space 229 (defined by the conformable frame) and onto the wound. Water is collected through return tube 230 through suction ports 231 and appropriate suction pump 232 and collected in wastewater tank 233. Water may be collected through a discrete segment of the tube formed integrally with an interior wall or plug 234 provided to isolate the supply and suction tubes. Alternatively, the suction tube may be butt-joined with the supply tube. Used fluid may also be collected with a second, discrete suction tube, or through an additional lumen and ports in the first tube.

Tube 221 may be made or formed in any cross section shape including but not limited to cylindrical, rectangular, trapaziodal or any other suitable shape. A suitable shape of tube 221 may be selected to control the flow of thermal energy around the wound, generally to increase the temperature of the wound site, however cooling may also be provided. Tube 221 may also include one or more insulating layers to control the thermal energy and prevent unwanted losses. Adhesive may also be used as necessary on tube or its adjacent surfaces to secure tube 221 in use.

In use, the devices of FIGS. 29 and 30 are applied to a patient so that the conformable tubing substantially circumscribes a wound, and fixed to the skin of the patient with adhesives on the cutaneous surfaces of the conformable tubing and absorbent ring (or secured with bandages, wherever adhesives are inadequate or inappropriate). The pump and heater are operated to maintain warm fluid flow through the tube, to maintain a warm environment proximate the wound. In the closed system of FIG. 29, the fluid is returned to reservoir, reheated and re-circulated through the system. When using the device of FIG. 30, the suction pump is operated to draw fluid from the wound environment and deliver that fluid to the wastewater tank. Therapeutic agents such as antibiotics may be added to the warm water source when medically indicated.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A shield for protecting a wound, the shield comprising:
   a conformable frame configured to circumscribe the wound;
   a first adhesive layer securing the conformable frame around the wound;
   a lid engaging the conformable frame to enclose a space about the wound;
   a second adhesive layer securing the lid to the conformable frame; and
   a vacuum device connected to the lid and configured to create a vacuum within the enclosed space,
   wherein the conformable frame comprises an absorbent layer for absorbing wound exudate.

2. The shield of claim 1, further comprising a vacuum adapter between the lid and the vacuum device.

3. The shield of claim 1, wherein the lid is configured to adapt to the vacuum device.

4. The shield of claim 1, wherein the vacuum device is located on the lid.

5. The shield of claim 1, wherein the vacuum device is configured to create a partial vacuum within the enclosed space.

6. The shield of claim 1, wherein the conformable frame comprises an elongated strip of exudate-absorbing material.

7. The shield of claim 1, wherein the conformable frame comprises multiple layers.

8. The shield of claim 1, wherein the conformable frame comprises a moisture-impermeable material.

9. A method of protecting a wound, the shield comprising:
   circumscribing the wound with a conformable frame;
   securing the conformable frame around the wound with a first adhesive layer;
   engaging the conformable frame with a lid to enclose a space about the wound;
   securing the lid to the conformable frame with a second adhesive layer;
   providing a vacuum device in operable communication with the lid; and
   creating a vacuum within the enclosed space with the connected vacuum device,
   wherein the conformable frame comprises an absorbent layer for absorbing wound exudate.

10. The method of claim 9, comprising connecting the vacuum device to a vacuum adapter connected to the lid.

11. The method of claim 9, comprising connecting the vacuum device directly to the lid.

12. The method of claim 9, wherein the vacuum device is located on the lid.

13. The method of claim 9, wherein the vacuum is a partial vacuum.

14. The method of claim 9, wherein the conformable frame comprises an elongated strip of exudate-absorbing material.

15. The method of claim 9, wherein the conformable frame comprises multiple layers.

16. The method of claim 9, wherein the conformable frame comprises a moisture-impermeable material.

* * * * *